(12) United States Patent
Stockhamer

(10) Patent No.: US 8,091,552 B2
(45) Date of Patent: Jan. 10, 2012

(54) APPARATUS TO MITIGATE THE SPREAD OF INFECTIOUS MATERIAL CAUSED BY COUGHING OR SNEEZING

(76) Inventor: Lee D. Stockhamer, Mohegan Lake, NY (US)

(*) Notice: Subject to any disclaimer, the term of this patent is extended or adjusted under 35 U.S.C. 154(b) by 289 days.

(21) Appl. No.: 12/424,866

(22) Filed: Apr. 16, 2009

(65) Prior Publication Data

US 2010/0263679 A1    Oct. 21, 2010

(51) Int. Cl.
- A62B 23/02 (2006.01)
- A41D 13/00 (2006.01)
- G07F 11/06 (2006.01)

(52) U.S. Cl. ............ 128/206.19; 128/863; 2/69; 221/85

(58) Field of Classification Search ............ 128/206.21, 128/206.28, 207.13, 205.24, 205.25, 205.27–206.19, 128/201.22–201.25, 206.23–206.26; 2/69, 2/160, 170, 16, 171, 910, 161, 6; 221/185, 221/85

See application file for complete search history.

(56) References Cited

U.S. PATENT DOCUMENTS

| | | |
|---|---|---|
| 4,244,057 A | 1/1981 | Burnham |
| 4,536,889 A | 8/1985 | Taylor et al. |
| 7,690,050 B2 * | 4/2010 | Stockhamer .................. 2/69 |
| 2004/0161450 A1 | 8/2004 | Buder |
| 2004/0250969 A1 | 12/2004 | Luu et al. |
| 2005/0129897 A1 | 6/2005 | Zhou et al. |
| 2005/0194010 A1 * | 9/2005 | Sankot .................. 128/206.19 |
| 2006/0225739 A1 * | 10/2006 | Rylander .................. 128/206.19 |
| 2006/0254591 A1 * | 11/2006 | Marx .................. 128/206.19 |
| 2009/0145445 A1 * | 6/2009 | Quinn .................. 128/863 |

* cited by examiner

Primary Examiner — Patricia Bianco
Assistant Examiner — Tarla Patel
(74) Attorney, Agent, or Firm — Hoffman & Baron, LLP

(57) ABSTRACT

Apparatus and method to mitigate the spread of infectious material caused by coughing or sneezing are disclosed. The apparatus includes a bottom, a peripheral first duct and a peripheral second duct, and a top. The bottom has a first side and an opposing second side. The peripheral first duct is disposed on the first side of the bottom and around a portion of the periphery of the bottom. The peripheral second duct is disposed on the first side of the bottom and around a second portion of the periphery of the bottom. The peripheral first duct has a first cavity and the peripheral second duct has a second cavity. The top includes at least one opening configured to receive a nose and mouth of a user. The top is disposed above the first side of the bottom and is recessed below the peripheral first duct and the peripheral second duct. The bottom, the top, the peripheral first duct and the peripheral second duct define a third cavity. The third cavity is in operational communication with said first cavity and said second cavity.

28 Claims, 4 Drawing Sheets

APPARATUS TO MITIGATE THE SPREAD OF INFECTIOUS MATERIAL CAUSED BY COUGHING OR SNEEZING

BACKGROUND OF THE INVENTION

The present application relates generally to devices for receiving the byproducts of coughing or sneezing. More specifically, the present application is directed to an apparatus to mitigate the spread of infectious material caused by coughing or sneezing.

In the health care field and other fields (e.g., food preparation field), as well as in everyday life, the practice of reducing the spread of infectious material (e.g., bacteria, viruses, mucous, germs, saliva, and other infectious material) that results from coughing or sneezing has become increasingly important. Many are sickened, some seriously and even fatally, from the infectious material spread by a sneeze or a cough. Government and private insurers have begun denying reimbursement to hospitals for the treatment of "preventable infections" that patients acquire in the hospitals.

The United States Centers for Disease Control and Prevention (CDC) and the Department of Health and Human Services (HHS) recommends reducing the spread of such infectious material by promoting the practice of "respiratory etiquette" (e.g., covering one's nose and mouth when coughing or sneezing). Because the common practice of covering one's nose and mouth with one's hand when coughing or sneezing results in hand and object contamination, the CDC and the HHS, among other things, instruct people to cover their nose and mouth regions using a conventional tissue or a clothing sleeve when coughing or sneezing in order to better restrain the infectious material or byproducts of a cough or a sneeze from spreading to others. Most people do not want to or are unable to cough or sneeze into a sleeve because there is a social constraint against using the sleeve as a tissue, coughing or sneezing into the sleeve contaminates the sleeve with infectious material, there may be no sleeve into which to cough or sneeze (e.g., short sleeve or sleeveless clothing), and coughing or sneezing into the sleeve may stain the sleeve (e.g., lipstick).

Often, the cough or the sneeze can occur with little warning, generally leaving insufficient time to react to the cough or the sneeze, such as by obtaining and using a conventional tissue to receive (e.g., block and/or capture) the infectious material or byproducts associated with the cough or the sneeze. The act of sneezing (sternutation) can expel the infectious material or the byproducts from one's nose and mouth region in excess of 100 miles per hour. Attempting to stifle sternutation, especially repeatedly, can cause serious injuries, such as damaged blood vessels, broken facial bones, as well as other serious injuries, and is not a viable alternative.

In some fields, it is often impractical or impossible to make the conventional tissue readily available. For example, in the health care field, a doctor or a nurse examining a patient, or a staff person carrying a tray, may not have free use of his or her hands to secure a tissue and to block the infectious material or byproducts associated with the cough or the sneeze. Even if a conventional tissue is readily available and its use not impractical or impossible, the conventional tissue may not sufficiently restrain the spread of the infectious material or byproducts expelled, often simply re-directing the infectious material expelled as a result of a cough or a sneeze. Furthermore, the cougher or sneezer's hand is often contaminated because the infectious material or byproducts expelled soak or blow through the tissue.

SUMMARY OF THE INVENTION

The present invention is an apparatus to mitigate the spread of infectious material or byproducts resulting from coughing or sneezing. The apparatus includes a bottom, a peripheral first duct and a peripheral second duct, and a top.

The bottom of the apparatus has a first side and an opposing second side. The peripheral first duct is disposed on the first side of the bottom and around a portion of the periphery of the bottom. The peripheral second duct is disposed on the first side of the bottom and around a second portion of the periphery of the bottom. The peripheral first duct has a first cavity and the peripheral second duct has a second cavity.

The top of the apparatus includes at least one opening to receive a nose and mouth of a user. The top is disposed above the first side of the bottom and is recessed below the peripheral first duct and the peripheral second duct. The bottom, the top, the peripheral first duct and the peripheral second duct define a third cavity. The third cavity is in operational communication with the first cavity and the second cavity.

The at least one opening of the top can include a nose opening to receive the nose of the user and a mouth opening to receive the mouth of the user. The nose opening and the mouth opening can be spaced apart or can form parts of a single opening through the top of the apparatus.

The top, bottom and sections of the peripheral first duct and peripheral second duct of the apparatus can be non-permeable to restrain exit of air expelled by the user through the at least one opening of the top. Non-permeability can be provided by chemical or thermo treatment of these components or construction of these components from a non-permeable material or materials. Additionally, the peripheral first duct and the peripheral second duct can include at least one permeable section to allow exit or channeling of air expelled by the user through desired sections of the apparatus.

The bottom of the apparatus can include a crease between the peripheral first duct and the peripheral second duct to allow folding of the apparatus. Specifically, when the apparatus is folded, such as in a crease of the user's hand or elbow, from a first position to a second position about the crease, the peripheral first duct and the peripheral second duct form a continuous boundary to seal around the user's nose and mouth. Additionally, the peripheral first duct and the peripheral second duct can further include respective raised portions contoured to seal around a nostril gap of the user's nose and other facial contours.

The present invention also includes a method of mitigating the spread of infectious material or byproducts resulting from coughing or sneezing. In accordance with the method, byproducts of a person's cough or a sneeze are received through at least one opening into a cavity of an apparatus defined by a top, a bottom and a plurality of peripheral ducts. The plurality of peripheral ducts defines respective cavities that are in operational communication with the cavity.

The received byproducts are filtered in the cavity and the respective cavities to generate filtered air that exits from the respective cavities through one or more permeable portions of the peripheral ducts. The filtered air can be restrained from exiting the respective cavities through one or more non-permeable portions of the peripheral ducts. The filtered air can further be restrained from exiting the cavity through the non-permeable top and bottom.

The person folds the plurality of peripheral ducts of the apparatus about a crease in the bottom between the ducts to form a continuous funnel-shaped periphery about the bottom. In a case where the apparatus is attached to a crease of the person's elbow, bending the elbow towards the person's nose and mouth automatically folds the peripheral ducts to form the funnel-shaped periphery. Similarly, the funnel-shaped periphery can be accomplished in a case where the apparatus that is situated in a crease of the person's hand is brought towards the person's nose and mouth. The funnel-shaped periphery seals about the person's nose and mouth region when person's nose and mouth region are received in conformity with the at least one opening of the apparatus.

Pressure produced by a sneeze or cough can expand one or more components of the apparatus (e.g., peripheral ducts), resulting in an improved seal of the apparatus about the person's nose and mouth region. The improved seal can be particularly useful if the apparatus is used in a non-folded or not fully folded manner such as when the apparatus is disposed on a portion of the person's arm that does not bend (e.g., forearm) or cannot bend sufficiently (e.g., shoulder/arm area) to fully form the funnel-shaped periphery.

The apparatus and method mitigate the spread of infectious material or byproducts resulting from a person coughing or sneezing. The construction and use of the apparatus reduce significantly the contamination of the surrounding area— including the person's hands, sleeves and the general vicinity around the person—with infectious material or byproducts associated with the person's cough or sneeze.

For a more thorough understanding of the present invention, reference is made to the following description, taken in conjunction with the accompanying drawings, and its scope will be pointed out in the appended claims.

BRIEF DESCRIPTION OF THE DRAWINGS

Some embodiments are illustrated by way of example and not limitation in the figures of the accompanying drawings in which.

DETAILED DESCRIPTION

An apparatus and a method of mitigating the spread of infectious material caused by a cough or a sneeze are disclosed. In the following description, for the purposes of explanation, numerous specific details are set forth in order to provide a thorough understanding of example embodiments. It will be evident, however, to one skilled in the art, that an example embodiment can be practiced without all of the disclosed specific details.

Figure 1:
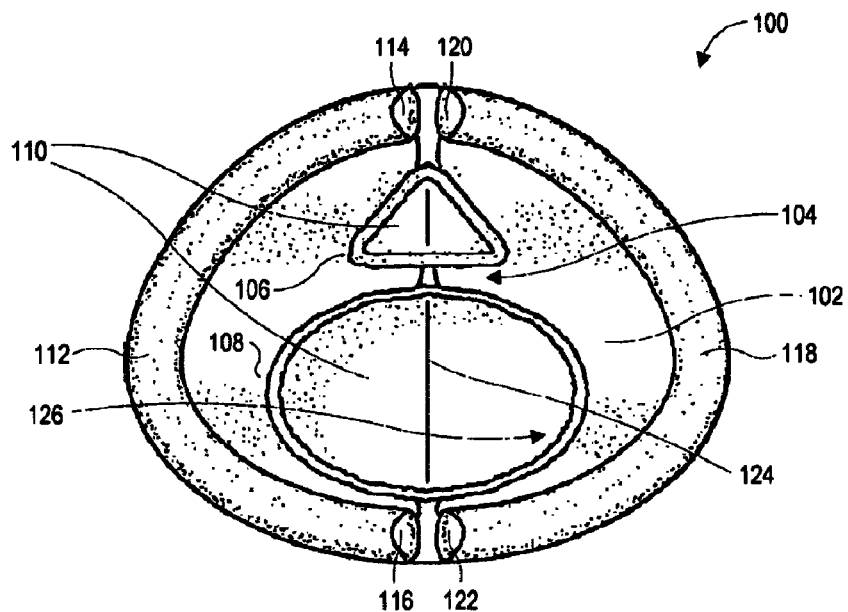
FIG. 1 illustrates a top view of a first embodiment of an example apparatus configured to mitigate the spread of infection material caused by coughing or sneezing.

FIG. 1 illustrates a top view of a first embodiment of an example apparatus 100 configured to mitigate the spread of infectious material caused by coughing or sneezing. The example apparatus 100 has a configuration that conforms to and seals around a person's nose and mouth region. More specifically, the example apparatus 100 of FIG. 1 has substantially elliptical lower portion that conforms to a person's mouth region and a substantially triangular-circular upper portion that conforms to the person's nose region. Other configurations that are adapted to conform to and seal around the person's nose and mouth region can be used.

The example apparatus 100 of FIG. 1 includes a top 102, a bottom 110, a peripheral first duct 112 and a peripheral second duct 118. The top 102 is recessed in relation to and surrounded by the peripheral first duct 112 and the peripheral second duct 118 to facilitate the peripheral ducts 112, 118 to seal around the person's nose and mouth region when the person's nose and mouth region is received in conformity with the example apparatus 100 of FIG. 1. A cavity 126 is bounded by the top 102, the bottom 110 and the peripheral ducts 112, 118. The cavity 126 communicates with or is open to the peripheral ducts 112, 118, which define respective cavities (not shown).

The example apparatus 100 can be constructed from a filtering material that is configured to filter the byproducts of a cough or a sneeze and further configured to allow filtered air to exit through the filtering material to the outside of the example apparatus 100. The filtering material can be an anti-microbial material that is configured to provide reusability of the example apparatus 100. The filtering material can be a cellulose-based material, or a combination of one or more materials that can provide moisture absorption, moisture channelling, antimicrobial properties, as well as other filtering properties. For example, the example apparatus 100 can be constructed from ST3225 (Foss Mfg. LLC of Hampton, N.H.), which includes Ecofi® polyester for moisture channelling, Fosshield® for anti-microbial properties and Rayon for absorption. In such a construction, the top 102 and bottom 100 can be chemically or thermo treated to make the top 102 and bottom 110 impermeable. Other elements, such as portions or sections of the peripheral ducts 112, 118 of the example apparatus 100 can further be chemically or thermo treated to make these elements impermeable, as will be described in greater detail below.

Alternatively, the example apparatus 100 can be constructed from an impermeable material, such as flexible plastic, vinyl, thermoformed polyester, or other non-permeable material. In such a construction, the filtering material, such as described above, can be disposed in or can line the cavity 126 (top 102 and bottom 110) and the peripheral ducts 112, 118. Additionally, an anti-microbial chemical treatment can be deposited on the top 102 and, in some embodiments on the peripheral ducts 112, 118, for reusability of the example apparatus 100. The anti-microbial chemical treatment is configured to mitigate infectious material on the top 102 and the peripheral ducts 112, 118 of the example apparatus 100.

The top 102 of the example apparatus 100 includes a nose and mouth receiving region 104 that is configured to receive the person's nose and mouth in conformity with the example apparatus 100 of FIG. 1. More specifically, the nose and mouth receiving region 104 includes at least one receiving opening in the top 102 that is configured to receive the person's nose (e.g., person's nostrils) and mouth in conformity with the example apparatus 100 of FIG. 1. The peripheral ducts 112, 118, as well as other elements of the example apparatus 100, can be perforated to allow filtered air to exit in a desired direction through these elements to the outside of the example apparatus 100.

The nose and mouth receiving region 104 of the top 102 includes a nose receiving opening 106 in the top 102 configured to receive the person's nose (e.g., nostril region of the nose). More specifically, the nose receiving opening 106 can be configured to receive the lower part of the person's nose, e.g., the nostril region. The nose receiving opening 106 has a configuration that is substantially triangular. Other configurations of the nose receiving opening 106 that are configured to conform to the person's nose (e.g., nostril region of the nose) can be used.

The nose and mouth receiving region 104 further includes a mouth receiving opening 108 in the top 102 that is disposed adjacently to the nose receiving opening 106. The mouth receiving opening 108 is configured to receive the person's mouth. The mouth receiving opening 108 has a configuration that is substantially elliptical. Other configurations of mouth receiving opening 108 that are configured to conform to the person's mouth can be used. For example, the mouth receiving opening 108 can be substantially round. The nose receiving opening 106 and mouth receiving opening 108 can be in communication (e.g., the periphery of the nose receiving opening 106 can break the periphery of mouth receiving opening 108), forming a single opening.

The bottom 110 of the example apparatus 100 includes a crease 124 configured to facilitate a partial folding of the example apparatus 100 about the crease 124 from a first open position to a second partially closed position, as is more clearly described with reference to FIGS. 3, 8 and 9 below.

The peripheral ducts 112, 114 are of arcuate configurations and the peripheral ducts 112, 114 extend about the periphery of the example apparatus 100 of FIG. 1. The peripheral first duct 112 includes a sloped first end 114 and an opposing sloped second end 116, and the peripheral second duct 118 includes a sloped first end 120 and an opposing second sloped end 122. The sloped first ends 114, 120 of the respective peripheral ducts 112, 118 are adjacent but spaced apart from one another. Similarly, the sloped second ends 116, 122 of the respective peripheral ducts 112, 118 are also adjacent but spaced apart from one another. The sloped ends 114, 116, 120 and 122 are closed. The sloped opposing sloped ends 114, 116 of the first peripheral duct 112 and the opposed sloped ends 120, 122 of the second peripheral duct 118 are configured to provide a continuous seal around the person's nose and mouth region when the example apparatus 100 is folded about the crease 124 from the first open position to the second partially closed position, described with reference to FIGS. 3, 8 and 9 below.

In operation, a person secures the example apparatus 100 to a crease in the person's elbow, or holds the example apparatus 100 in a crease of person's hand. Upon sensing an oncoming cough or sneeze, the person advances the elbow or the hand to the person's nose and mouth region and positions the nose and mouth region in conformity with the example apparatus 100 (e.g., pressing the person's nose and mouth region in conformity with the nose and mouth receiving region 104 of the example apparatus 100). The example apparatus 100 folds about crease 124 and seals around the person's nose and mouth region. More specifically, the peripheral ducts 112, 118 create a continuous boundary (e.g., funnel-shaped periphery) configured to seal around the nose and the mouth of a person. The person coughs or sneezes into the example apparatus 100 through the nose and mouth receiving region 104. Pressure produced by a sneeze or cough can expand one or more components of the example apparatus 100 (e.g., peripheral ducts 112, 118), resulting in an improved seal of the example apparatus 100 about the person's nose and mouth region 104. The improved seal can be particularly useful if the example apparatus 100 is used in a non-folded or not fully folded manner such as when the example apparatus 100 is disposed on a portion of the person's arm that does not bend (e.g., forearm) or cannot bend sufficiently (e.g., shoulder/arm area) to fully form the funnel-shaped periphery.

Further with regard to the operation, the example apparatus 100 receives the byproducts of the person's cough or sneeze. The forceful expulsion of the byproducts disperses the byproducts through the interior of the example apparatus 100 (e.g., cavity 126 and respective cavities of peripheral ducts 112, 118). The received byproducts are filtered in the cavity 126 and the respective cavities of the peripheral ducts 112, 118 to generate filtered air. The filtered air exits from the example apparatus 100 through one or more permeable portions or sections of the peripheral ducts 112, 118. The filtered air can be restrained from exiting through one or more non-permeable portions of the peripheral ducts 112, 118 and non-permeable 102 top and bottom 110. Thereafter, the example apparatus 100 can be discarded, or the example apparatus 100 can be reused if it is made of an anti-microbial material or an anti-microbial chemical treatment is applied to the top 102, particularly if an insubstantial amount of the byproducts is expelled by the person's cough or sneeze.

Figure 2:
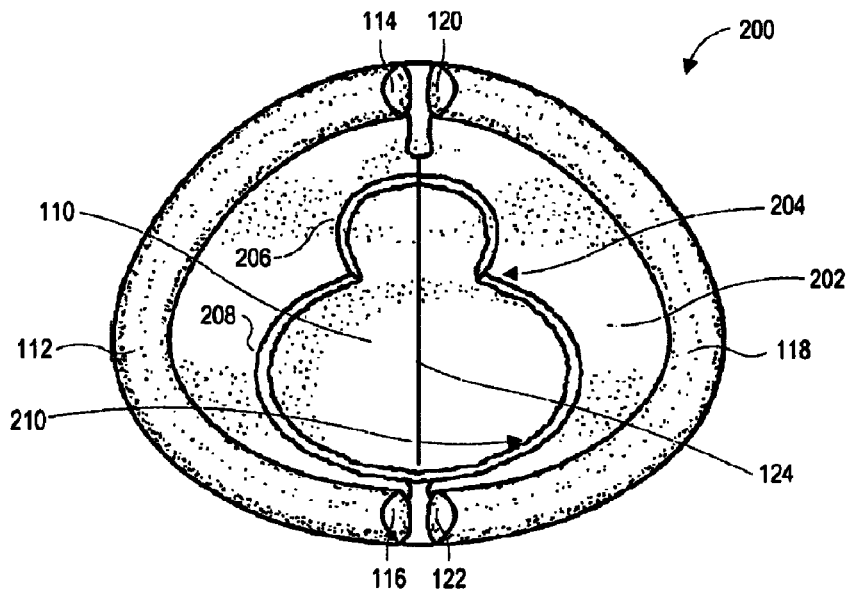
FIG. 2 illustrates a top view of a second embodiment of an example apparatus configured to mitigate the spread of infectious material caused by coughing or sneezing.

FIG. 2 illustrates a top view of a second embodiment of an example apparatus 200 configured to mitigate the spread of infectious material caused by coughing or sneezing. The example apparatus 200 is similar to the example apparatus 100 of FIG. 1 described above. The example apparatus 200 has a configuration that conforms to and seals around a person's nose and mouth region. More specifically, the example apparatus 200 of FIG. 2 has a substantially elliptical lower portion that conforms to a person's mouth region and a substantially triangular-circular upper portion that conforms to the person's nose region. Other configurations that are adapted to conform to and seal around the person's nose and mouth region can be used.

The example apparatus 200 of FIG. 2 includes a top 202, a bottom 110, a peripheral first duct 112 and a peripheral second duct 118. The top 202 is recessed in relation to and surrounded by the peripheral first duct 112 and the peripheral second duct 118 to facilitate the peripheral ducts 112, 114 to seal around the person's nose and mouth region when the person's nose and mouth region is received in conformity with a nose and mouth receiving region 204 of the example apparatus 200 of FIG. 2. A cavity 210 is bounded by the top 102, the bottom 110 and the peripheral ducts 112, 114. The cavity 210 communicates with or is open to the peripheral ducts 112, 118, which define respective cavities (not shown).

The top 202 includes the nose and mouth receiving region 204 that is configured to receive the person's nose and mouth. The nose and mouth receiving region 204 includes at least one receiving opening in the top 202 that is configured to receive the person's nose and mouth.

More specifically, the nose and mouth receiving region 204 of the top 202 includes a nose receiving opening 206 in the top 202 configured to receive the person's nose. The nose receiving opening 206 has a configuration that is substantially oval. Other configurations of the nose receiving opening 206 that are configured to conform to the person's nose can be used.

For example, the nose receiving opening 206 can be triangular, circular or elliptical, as we well as any other configuration.

The nose and mouth receiving region 204 further includes a mouth receiving opening 208 in the top 202 that is disposed in communication with the nose receiving opening 206 (e.g., the periphery of nose receiving opening 206 breaks the periphery of mouth receiving opening 208), forming a single opening. The mouth receiving opening 208 is configured to receive the person's mouth. The mouth receiving opening 208 has a configuration that is substantially elliptical. Other configurations of mouth receiving opening 208 that are configured to conform to the person's mouth can be used.

Figure 3:
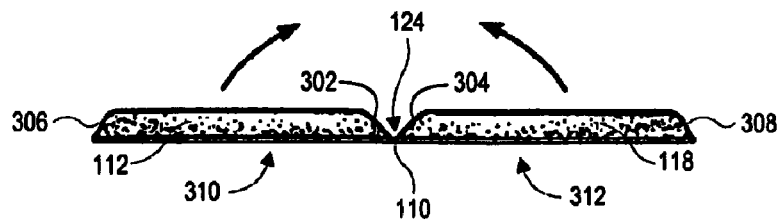
FIG. 3 illustrates a side view of the example apparatuses of FIGS. 1 and 2.

FIG. 3 illustrates a side view of the example apparatuses 100, 200 of FIGS. 1 and 2, respectively. A first outer wall 306 of the peripheral first duct 112 and a second outer wall 308 of the peripheral second duct 118 are configured to extend substantially upward from the bottom 110. The first outer wall 306 and the second outer wall 308 are further configured to slope toward the interior of the example apparatuses 100, 200. The first ends 114, 120 of the peripheral ducts 112, 118 have sloped end walls 302, 304 that slope downward and inward toward the crease 124. Similarly, the second ends 116, 122 of the peripheral ducts 112, 118 have sloped end walls 302, 304 that slope downward and inward toward the crease 124.

As shown in the side view of FIG. 3, the crease 124 is configured to facilitate a partial folding of the example apparatuses 100, 200 about the crease 124 from a first open position to a second partially closed position, as indicated by the thick arrows. More specifically, a first half 310 of the example apparatuses 100, 200 folds about the crease 124 along a travel path indicated by the left thick arrow, while a second half 312 of the example apparatus 100, 200 folds about the crease 124 along a travel path indicated by the right thick arrow. In the second partially closed position (shown in FIG. 9), sloped end walls 302, 304 of first ends 114, 120 and sloped end walls 302, 304 of the second ends 116, 122 are disposed adjacent each other and are configured to seal the peripheral first duct 112 and the peripheral second duct 118, respectively, around the person's nose and mouth region.

Figure 4:
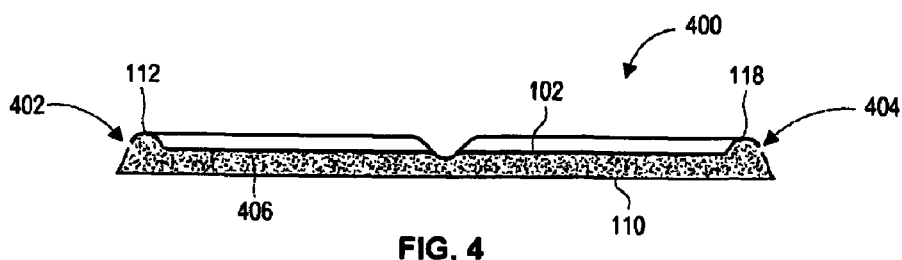
FIG. 4 illustrates a cross-sectional view of the example apparatuses of FIGS. 1 and 2 of a first example construction.

FIG. 4 illustrates a cross-sectional view of the example apparatuses 100, 200 of FIGS. 1 and 2 of a first example construction 400. Although the first example construction 400 is described with reference to the example apparatus 100 of FIG. 1, the first example construction 400 applies similarly to the example apparatus 200 of FIG. 2. The first example construction 400 illustrates the example apparatus 100, constructed from a filtering material 406 (e.g., a cellulose-based or combination filtering material described with reference to FIG. 1) that is configured to filter the byproducts of a cough or a sneeze, and further treated to channel the byproducts and allow filtered air to exit through sections of the filtering material 406 to the outside of the example apparatus 100. In the first example construction 400, the top 102 and bottom 100 are treated (e.g., chemically or thermally) and thus non-permeable. Portions or sections of the peripheral ducts 112, 118 are also treated (e.g., chemically or thermally) and thus non-permeable. One or more sections 402 of peripheral first duct 112 and one or more sections 404 of peripheral second duct 118 are untreated and thus permeable. The treatment of the top 102, bottom 110, and sections of the ducts 112, 118 facilitates the channelling and filtration of the byproducts over a greater area of the filtering material 406 and the exiting of the filtered air in a desired direction to the outside of the example apparatus 100 through sections 402, 404.

Figure 5:
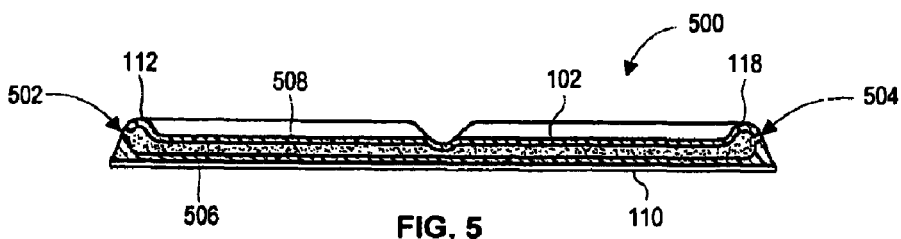
FIG. 5 illustrates another cross-sectional view of the example apparatuses of FIGS. 1 and 2 of a second example construction.

FIG. 5 illustrates a cross-sectional view of the example apparatuses 100, 200 of FIGS. 1 and 2 of a second example construction 500. Although the example construction 500 is described with reference to the example apparatus 100 of FIG. 1, the example construction 500 applies similarly to the example apparatus 200 of FIG. 2. The example construction 500 illustrates the example apparatus 100, constructed from an impermeable material, such as flexible plastic, vinyl, thermoformed polyester, or other non-permeable material. Filtering material 506, 508 (e.g., cellulose-based or combination filtering material described with reference to FIG. 1) that is configured to filter the byproducts of a cough or a sneeze is disposed in the example apparatus 100, lining the bottom 110, the top 102 and the peripheral ducts 112, 118. In the example construction 500, one or more sections 502 of peripheral first duct 112 and one or more sections 504 of peripheral second duct 118 are perforated to facilitate the channelling and filtration of the byproducts over a greater area of the filtering material 506, 508 and the exiting of the filtered air to the outside of the example apparatus 100 through sections 502, 504.

Figure 6:
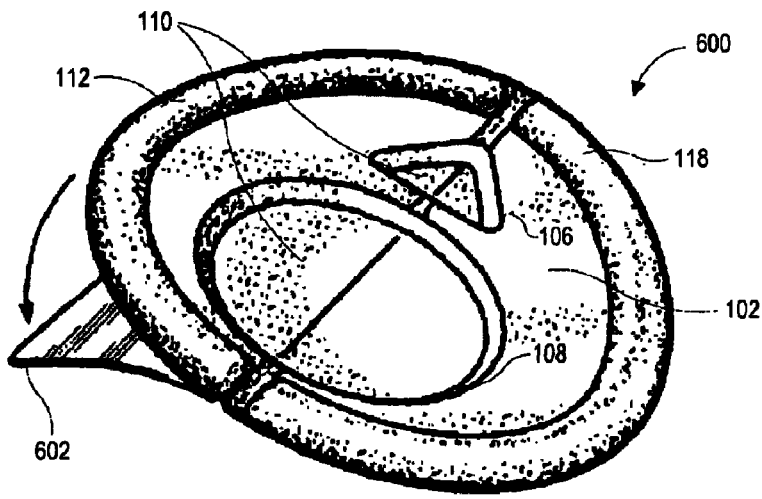
FIG. 6 illustrates a top elevational view of a third embodiment of an example apparatus configured to mitigate the spread of infectious material caused by coughing or sneezing.

FIG. 6 illustrates a top elevational view of a third embodiment of an example apparatus 400 configured to mitigate the spread of infectious material caused by coughing or sneezing. The example apparatus 600 of FIG. can be similar to the example apparatuses 100, 200 of FIGS. 1 and 2, described above. The example apparatus 600 includes a backing 602 that is removably adhered to the bottom 110. The backing 602 can be removed (peeled off) from the bottom 110 of the example apparatus 600 as indicated by an arrow pointing away from the example apparatus 600.

Figure 7:
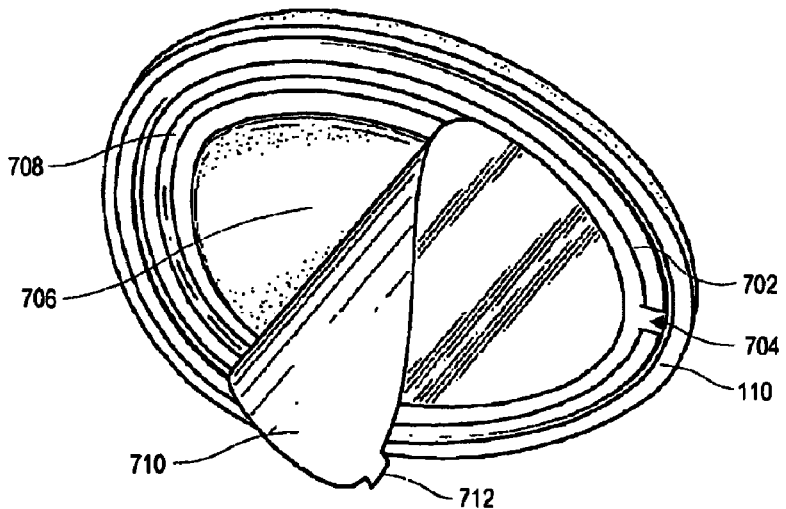
FIG. 7 illustrates a bottom elevational view of the example apparatus of FIG. 6.

FIG. 7 illustrates a bottom elevational view of the example apparatus 600 of FIG. 6, with the backing 602 removed. The bottom 110 includes an adhesive strip 702 that is disposed at least partially around the periphery of the bottom 110. The adhesive strip 702 is configured to removably secure the backing 602 to the example apparatus 600 of FIG. 6. At least one gap 704 can be provided along the adhesive strip 702 to facilitate the removal of the backing 602 from the bottom 110 of the example apparatus 600. The adhesive strip 702 is further configured to removably adhere to an arm, a hand or an article of clothing after the removal of the backing 602. In one embodiment, the example apparatus 600 includes an anti-microbial wipe 706 disposed on the bottom 110 to the interior of the adhesive strip 702. A wipe cover 710 is removably adhered to the bottom 110 via an adhesive strip 708. The wipe cover 710 provides a tab 712 for easier removal from bottom 110.

The anti-microbial wipe 706 can be accessed and used after sneezing or coughing into the example apparatus 600 by peeling off the example apparatus 600 from the elbow, lifting from beneath one or more of the peripheral ducts 112, 118 to mitigate hand contamination, and folding the example apparatus 600 closed along the crease 124 to further mitigate hand and object contamination. Similarly, the example apparatus 600 can be folded along the crease 124 if it were used in the crease of the hand. Thereafter, the wipe cover 710 can be peeled back or off using tab 712 to expose the anti-microbial wipe 706. The anti-microbial wipe 706 can be removed and a first side of the anti-microbial wipe 706 can be used to clean the person's nose and mouth region to mitigate contamination. Once the first side is used, the anti-microbial wipe 706 with the first side facing in can then be wrapped around the folded example apparatus 600 and second side of the anti-microbial wipe 706 now wrapped around the example apparatus can be used to wipe the person's hands to further mitigate contamination. Thereafter, the wrapped apparatus 600 can be thrown out.

Figure 8:
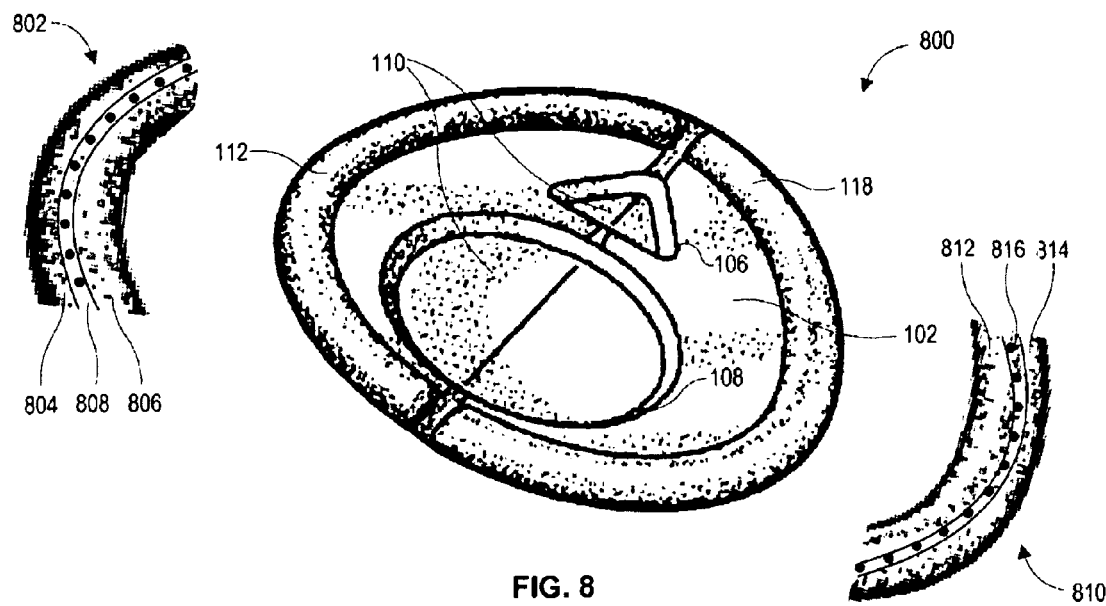
FIG. 8 illustrates a top elevational view of a fourth embodiment of an example apparatus configured to mitigate the spread of infectious material caused by coughing or sneezing.

FIG. 8 illustrates a top elevational view of a fourth embodiment of an example apparatus 800 configured to mitigate the spread of infectious material caused by coughing or sneezing. The example apparatus 800 of FIG. 8 can be similar to the example apparatuses 100, 200, 600 of FIGS. 1, 2, 6, described above. The example apparatus 800 of FIG. 8 illustrates a first exploded top portion 802 of the peripheral first duct 112 and a second exploded top portion 810 of the peripheral second duct 118.

The first exploded top portion 802 is configured to partially restrain air expelled through the nose opening 106 and the mouth opening 108 from exiting the peripheral first duct 112. The first exploded top portion 802 includes sections 804, 806, and 808. The sections 804, 806 are configured to restrain air expelled through the nose opening 106 and the mouth opening 108 from exiting the peripheral first duct 112, while the section 808 is configured to allow air expelled through the nose opening 106 and the mouth opening 108 to exit the peripheral first duct 112.

The sections 804, 806 (as well as top the 102 and the bottom 110) can be chemically or thermo treated to make them non-permeable when peripheral ducts 112, 118 (as well as the top 102 and the bottom 110) are made of a permeable filtering material (e.g., anti-microbial filtering material), while section 808 can remain untreated and thus remain permeable. Alternatively, the sections 804, 806 (as well as the top 102 and the bottom 110) can be non-permeable because they are formed of a non-permeable material (e.g., plastic, vinyl, thermoformed polyester), while section 808 can be made permeable by perforations in the non-permeable material of the peripheral first duct 112.

The second exploded top portion 810 is configured to partially restrain air expelled through the nose opening 106 and the mouth opening 108 from exiting the peripheral first duct 118. The second exploded top portion 810 includes sections 812, 814, and 816. The sections 812, 814 are configured to restrain air expelled through the nose opening 106 and the mouth opening 108 from exiting the peripheral second duct 118, while the section 616 is configured to allow air expelled through the nose opening 106 and the mouth opening 108 to exit the peripheral second duct 118.

The sections 812, 814 (as well as top the 102 and the bottom 110) can be chemically or thermo treated to make them non-permeable when ducts 112, 118 (as well as the top 102 and the bottom 110) are made of a permeable filtering material (e.g., anti-microbial filtering material), while section 816 can remain untreated and thus remain permeable. Alternatively, the sections 812, 814 (as well as the top 102 and the bottom 110) can be non-permeable because they are formed of a non-permeable material (e.g., plastic, vinyl, thermoformed polyester), while section 816 can be made permeable by perforations or micro-perforations in the non-permeable material of the peripheral second duct 118.

Figure 9:
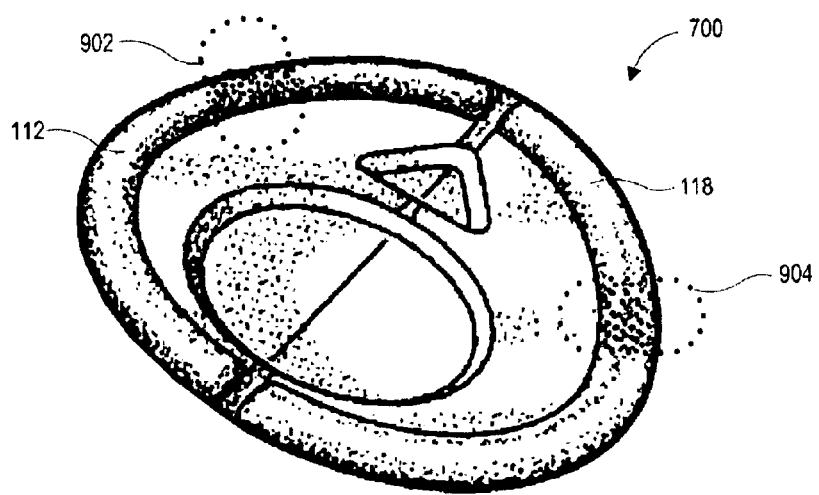
FIG. 9 illustrates a top elevational view of a fifth embodiment of an example apparatus configured to mitigate the spread of infectious material caused by coughing or sneezing.

FIG. 9 illustrates a top elevational view of a fifth embodiment of an example apparatus 900 configured to mitigate the spread of infectious material caused by coughing or sneezing. The example apparatus 900 of FIG. 9 can be similar to the example apparatuses 100, 200, 600, 800 of FIGS. 1, 2, 6, 8, described above. The example apparatus 900 of FIG. 9 illustrates a first raised and contoured portion 902 of the peripheral first duct 112 and a second raised and contoured portion 904 of the peripheral second duct 118. The raised and contoured portions 902, 904 are configured to provide a better seal around the person's nose (e.g., providing a better seal around the person's "nostril gap").

Figure 10:
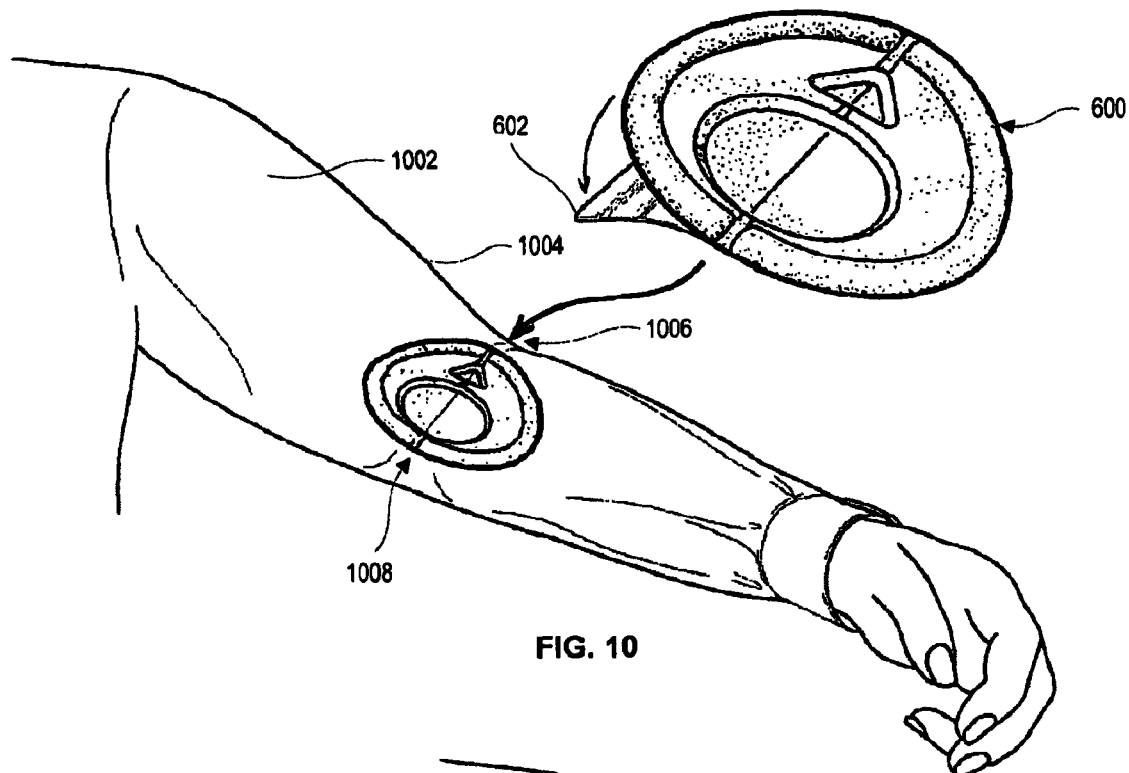
FIG. 10 illustrates example operation of an example apparatus of FIG. 6 in a first open position attached to a garment at a crease of a person's elbow.

FIG. 10 illustrates example operation of the example apparatus 600 FIG. 6 in a first open position 1008 attached to a garment 1004 at a crease of a person's elbow 1006. Other example embodiments of the apparatus illustrated in the drawings and described herein can be used similarly. As illustrated in FIG. 10, backing 602 is peeled off the example apparatus 600 and the example apparatus 600 is disposed in approximate conformity with the crease of the person's elbow 1006 when the person's arm 1002 is substantially extended (e.g., arm 1002 in substantial extension about the elbow 1006). More specifically, the crease 124 of the example apparatus 600 is disposed in approximate conformity with the crease of the person's elbow 1006. Once the example apparatus 600 is disposed about the crease of the person's elbow 1006, the person is able to perform ordinary tasks or duties required, as the example apparatus 600 does not limit the range of motion of the person's arm 1002. Upon the onset of a cough or sneeze, the person is thereafter able to use the example apparatus 600, even in circumstances when the person's hands are occupied.

Figure 11:
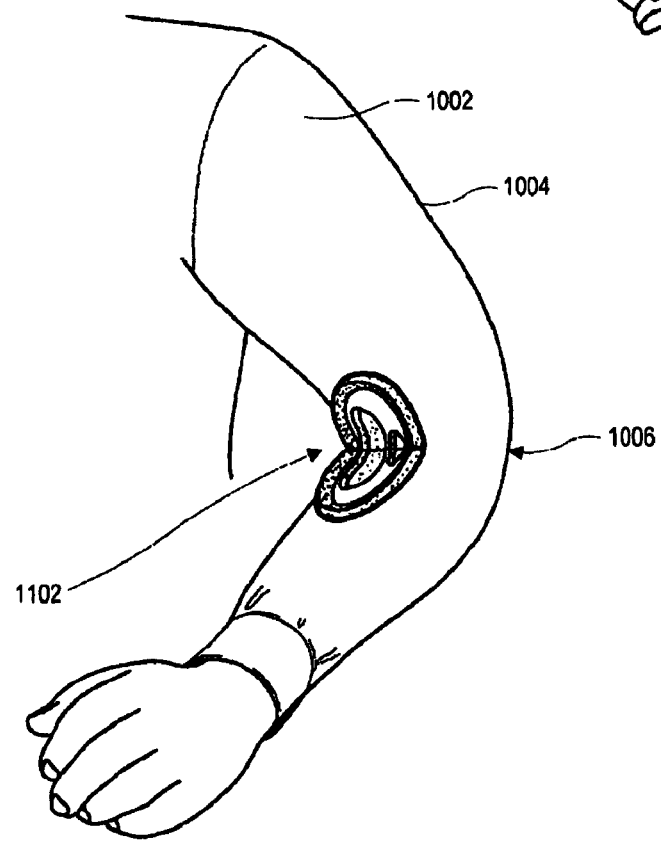
FIG. 11 illustrates example operation of the example apparatus of FIG. 6 illustrated in FIG. 10 in a second partially closed position attached to a garment at a crease of a person's elbow.

FIG. 11 illustrates example operation of the example apparatus 600 illustrated in FIG. 10 in a second partially closed position 1102 attached to a garment 1004 at a crease of a person's elbow 1006. As illustrated in FIG. 11, the example apparatus 600 folds into the second partially closed position 1102 in conformity with the flexion in the person's elbow 1006 (e.g., arm 102 in flexion about the elbow 106). The second partially closed position 1102 approximates a funnel shape to better seal against the person's nose and mouth region. Upon the onset of a cough or a sneeze, the person can flex the arm 1002 about the elbow 1006 from substantial extension of FIG. 10 into substantial flexion of FIG. 11, which in turn folds the example apparatus into the second partially closed position 1102 (e.g., funnel shape).

The person then advances the arm 1002 to the person's nose and mouth region and positions the nose and mouth region in conformity with the example apparatus 600 (e.g., in conformity with the nose and mouth receiving region 104 of the example apparatus 600). Similarly, the example apparatus 600 can be positioned in the crease of the person's hand and advanced to the person's nose and mouth region. The example apparatus 600 seals around the person's nose and mouth region. The person coughs or sneezes into the example apparatus 600. The example apparatus 600 receives the byproducts of the person's cough or sneeze. Thereafter, the example apparatus 600 can be removed from the arm 1102 and discarded or the anti-microbial wipe 706 of FIG. 7 can be used and then the apparatus 600 can be discarded. Alternatively, the example apparatus 600 can be reused (e.g., if made of anti-microbial material) without its removal from the arm 1102.

Thus, an apparatus and method of mitigating the spread of infectious material caused by a cough or a sneeze have been described. Although specific example embodiments have been described, it will be evident that various modifications and changes can be made to these embodiments without departing from the broader scope of this application. Accordingly, the specification and drawings are to be regarded in an illustrative rather than a restrictive sense. The accompanying drawings that form a part hereof, show by way of illustration, and not of limitation, specific embodiments in which the subject matter can be practiced. The embodiments illustrated are described in sufficient detail to enable those skilled in the art to practice the teachings disclosed herein. Other embodiments can be utilized and derived therefrom, such that structural substitutions and changes can be made without departing from the scope of this application. This Detailed Description, therefore, is not to be taken in a limiting sense, and the scope of various embodiments is defined only by the appended claims, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention, inventive concept or embodiment. Thus, although specific embodiments have been illustrated and described herein, it should be appreciated that any arrangement calculated to achieve the same purpose can be substituted for the specific embodiments shown. This application is intended to cover any and all adaptations or variations of various embodiments. Combinations of the above embodiments and other embodiments not specifically described herein, will be apparent to those of skill in the art upon reviewing the above description.

The Abstract is provided to comply with 37 C.F.R. §1.72(b) and will allow the reader to quickly ascertain the nature of the technical disclosure of this application. It is submitted with the understanding that it will not be used to interpret or limit the scope or meaning of the claims.

In the foregoing description of the embodiments, various features can be grouped together in a single embodiment for the purpose of streamlining the disclosure of this application. This method of disclosure is not to be interpreted as reflecting that the claimed embodiments have more features than are expressly recited in each claim. Rather, as the following claims reflect, inventive subject matter lies in less than all features of a single disclosed embodiment.

What is claimed is:

1. An apparatus to mitigate the spread of infectious material caused by coughing or sneezing, the apparatus comprising:
a bottom having a first side and an opposing second side, said bottom configured to fold from an open position to a partially folded position;
a peripheral first duct being disposed on said first side of said bottom and around a portion of the periphery of said bottom, said peripheral first duct having a first cavity;
a peripheral second duct being disposed on said first side of said bottom and around a second portion of the periphery of said bottom, said peripheral second duct having a second cavity; and
a top including at least one opening configured to receive a nose and mouth of a user, said top being disposed above said first side of said bottom and being recessed below said peripheral first duct and said peripheral second duct;
wherein said top, said bottom, said peripheral first duct and said peripheral second duct define a third cavity in operational communication with said first cavity and said second cavity, and
wherein said peripheral first duct and peripheral second duct form a continuous periphery configured to seal about the user's nose and mouth when said bottom is folded to the partially folded position.

2. The apparatus of claim 1, wherein said at least one opening of said top includes a nose opening configured to receive said nose of said user.

3. The apparatus of claim 2, wherein configuration of said nose opening is one selected from the group consisting of triangular, oval, and elliptical.

4. The apparatus of claim 2, wherein at least one opening of said top includes a mouth opening configured to receive said mouth of said user.

5. The apparatus of claim 4, wherein said nose opening and said mouth opening are spaced apart.

6. The apparatus of claim 4, wherein said nose opening and said mouth opening form a single opening.

7. The apparatus of claim 1, wherein at least one of said top, said bottom, a section of said peripheral first duct and a section of said peripheral second duct is non-permeable.

8. The apparatus of claim 1, wherein said top, said bottom, said peripheral first duct and said peripheral second duct are made from a filtering material that includes one or more materials.

9. The apparatus of claim 1, wherein said top, said bottom, said peripheral first duct and said peripheral second duct are made from impermeable material.

10. The apparatus of claim 9, wherein a filtering material is disposed within said first cavity, said second cavity and said third cavity.

11. The apparatus of claim 1, wherein at least one of said top, said bottom, peripheral first duct and said peripheral second duct is expandable from pressure produced by said coughing or sneezing.

12. The apparatus of claim 1, wherein an anti-microbial layer is deposited on said top.

13. The apparatus of claim 1, wherein at least one of said peripheral first duct and said peripheral second duct includes at least one non-permeable section configured to restrain exit of air expelled by said user through said at least one opening of said top.

14. The apparatus of claim 1, wherein at least one of said peripheral first duct and said peripheral second duct includes at least one permeable section configured to allow exit of air expelled by said user through said at least one opening of said top.

15. The apparatus of claim 1, wherein said peripheral first duct includes a first raised portion and said peripheral second duct includes a second raised portion, said first raised portion and said second raised portion contoured to seal around a nostril gap of said nose of said user.

16. The apparatus of claim 1, wherein said bottom includes a crease between said peripheral first duct and said peripheral second duct.

17. The apparatus of claim 16, wherein said peripheral first duct includes a first sloped end and a second sloped end, and said peripheral second duct includes a first sloped end and a second sloped end.

18. The apparatus of claim 16, wherein upon folding said bottom from a first position to a second position about said crease, said peripheral first duct and said peripheral second duct form a continuous boundary configured to seal around said nose and said mouth.

19. The apparatus of claim 16, wherein an adhesive is disposed on said second side of said bottom and around at least a portion of the periphery of said bottom, the adhesive configured to operatively attach said bottom to said user.

20. The apparatus of claim 1, further comprising a backing removably adhered to said second side of said bottom.

21. The apparatus of claim 1, further comprising a removably adhered anti-microbial wipe disposed on said second side of said bottom.

22. A method of mitigating the spread of infectious material caused by coughing or sneezing, the method comprising:
folding an apparatus defined by a top, a bottom and a plurality of peripheral ducts from an open position to a partially folded position in which said plurality of peripheral ducts form a continuous periphery about said bottom configured to seal about a person's nose and mouth when said apparatus is in the partially folded position;

receiving byproducts of a person's cough or a sneeze through at least one opening in the top into a cavity defined by said top, said bottom and said peripheral ducts, said cavity being in operational communication with cavities defined by the respective peripheral ducts; and filtering said byproducts in said cavity and said respective cavities to generate filtered air that exits from said respective cavities through one or more permeable portions of said plurality of peripheral ducts.

23. The method of claim 22, further comprising restraining exiting of said filtered air from said respective cavities through one or more non-permeable portions of said peripheral ducts.

24. The method of claim 22, further comprising restraining exiting of said filtered air from said cavity through said top and said bottom.

25. The method of claim 22, further comprising receiving a person's nose and mouth region in conformity with said at least one opening.

26. The method of claim 25, further comprising:
folding said plurality of peripheral ducts about a crease in said bottom between said plurality of peripheral ducts to form a continuous funnel-shaped periphery about said bottom; and
sealing the funnel-shaped periphery about said person's nose and mouth region.

27. The method of claim 22, expanding at least one of said top, said bottom, a peripheral first duct and a peripheral second duct of said plurality of peripheral ducts from pressure produced by said cough or sneeze.

28. The method of claim 22, further comprising removably adhering said bottom to said person's arm.

* * * * *